United States Patent [19]
Colwell et al.

[11] Patent Number: 5,686,299
[45] Date of Patent: Nov. 11, 1997

[54] METHOD AND APPARATUS FOR DETERMINING NUTRIENT STIMULATION OF BIOLOGICAL PROCESSES

[75] Inventors: Frederick S. Colwell, Idaho Falls, Id.; Gill G. Geesey; Richard J. Gillis, both of Bozeman, Mont.; R. Michael Lehman, Idaho Falls, Id.

[73] Assignee: Lockheed Idaho Technologies Company, Idaho Falls, Id.

[21] Appl. No.: 448,022

[22] Filed: May 23, 1995

[51] Int. Cl.$^6$ .............................. C12M 3/00; E21B 49/00
[52] U.S. Cl. .................... 435/287.1; 435/286.1; 435/289.1; 435/297.1; 435/304.1; 73/152.19; 73/152.23; 73/152.25; 73/23.41; 73/61.72; 73/863.23
[58] Field of Search ............................ 435/286.1, 287.1, 435/288.1, 289.1, 297.1, 304.1; 436/28; 73/152.19, 152.23, 152.25, 152.26, 152.28, 23.41, 61.72, 863.23

[56] References Cited

U.S. PATENT DOCUMENTS 5,221,159  6/1993  Billings et al. ................... 405/128

*Primary Examiner*—David A. Redding
*Attorney, Agent, or Firm*—Thorpe North & Western

[57] ABSTRACT

A method and apparatus for determining the nutrients to stimulate microorganisms in a particular environment. A representative sample of microorganisms from a particular environment are contacted with multiple support means wherein each support means has intimately associated with the surface of the support means a different nutrient composition for said microorganisms in said sample. The multiple support means is allowed to remain in contact with the microorganisms in the sample for a time period sufficient to measure differences in microorganism effects for the multiple support means. Microorganism effects for the multiple support means are then measured and compared. The invention is particularly adaptable to being conducted in situ. The additional steps of regulating nutrients added to the particular environment of microorganisms can enhance the desired results. Biological systems particularly suitable for this invention are bioremediation, biologically enhanced oil recovery, biological leaching of metals, and agricultural bioprocesses.

12 Claims, 5 Drawing Sheets

5,686,299

METHOD AND APPARATUS FOR DETERMINING NUTRIENT STIMULATION OF BIOLOGICAL PROCESSES

CONTRACTUAL ORIGIN OF THE INVENTION

The United States Government has rights in this invention disclosed under Contract Number DE-AC07-76ID01570 between the U.S. Department of Energy and EG&G Idaho, Inc., now Contract Number DE-AC07-94ID13223 with Lockheed Idaho Technologies Company.

BACKGROUND OF THE INVENTION

1. Field of Invention

The present invention relates generally to a method and apparatus for determining nutrient stimulation of biological processes. Such biological processes include bioremediation, biologically enhanced oil recovery, biological leaching of metals, and agricultural bioprocesses such as biological treatment of compost.

2. Background Art

Many biological processes depend upon nutrients to stimulate growth and activity of the microorganisms involved. These nutrients can be organic and/or inorganic materials. Organic materials such as acetate or citrates provide carbon for building new cell material or biomass, and/or energy. Inorganic materials such as nitrates and phosphates provide the nitrogen and phosphorous which are key building blocks for the cells.

An example of the role nutrients play in bioremediation processes is in the soil vapor extraction processes for remediating ground water contaminated with organic and inorganic materials. The processes described in Billings et al, U.S. Pat. No. 5,221,159 are illustrative. Billings et al. describes methods and processes for in situ removal of contaminants, such as organic and inorganic products, from soil and groundwater by providing one or more injection wells drilled to a depth below the water table and an extraction well drilled to a depth above the water table. Oxygenated gas is injected under pressure through the injection well while vacuum is applied to the extraction well. Most of the contaminants removed from the groundwater and vadose zone are due to biochemical processes. Microbes from the contaminated site are extracted and analyzed to determine the genera present in the samples. Microbes from genera known to be useful in biodegrading the contaminants are then isolated, and the isolated microbes are fermented to increase the numbers of useful organisms. Then the fermented microorganisms are reintroduced through the injection or extraction wells to enhance biodegradation. If necessary, because of low levels of contaminants and consequent low levels of microbes, nutrients are provided to the microbial population to sustain high levels of degradation activity. This method suffers from not knowing, except through trial and error, what nutrient composition should be added for the particular environment involved to enhance the in situ bioremediation that is key to the success of this technology.

A paper presented by the Cullimore et al at the First International Symposium on Microbiology of the Deep Subsurface in Jan. 15–19, 1990, entitled "Development Strategies for the Utilization of In-Well Incubation Devices (IWID) to Establish Management Strategies for the Bioremediation of Chemically Impaired Water Wells and Groundwater Systems" notes the problem of identifying the proper nutrient composition to facilitate the desired microbial activity in bioremediation processes. The solution proposed in this paper is to put a group of test tubes containing different nutrient compositions into the borehole and then adding samples of the contaminated water into the different test tubes. After a one month incubation period the test tubes are removed from the borehole and analyzed.

The Cullimore et al process for determining nutrient addition to stimulate microbial activity suffers from significant problems. First of all the process uses test tubes which measure only the free living (unattached) microbial communities. However, the free living microbial populations are in many systems much less significant than the attached microbial populations. One study is believed to have shown that biological activity from attached microbial populations was 100 times more significant than that due to free living microbial communities.

Another significant draw-back of the Cullimore et al approach is that the test is essentially a batch culture and thus the test would only represent the chemical conditions of the particular environment at the beginning of the test. Therefore, there are serious concerns about the commercial applicability of the Cullimore et al test.

SUMMARY OF THE INVENTION

It is an object of the present invention to provide a method and apparatus for determining nutrient stimulation of biological processes.

It is also an object of the invention to provide a method and apparatus for determining nutrient stimulation for attached microbial populations in a particular environment.

It is another object of the invention to provide a method and apparatus for in situ determination of nutrients suitable for stimulation of a desired microbial population in a particular biological system.

It is still another object of the invention to enhance the desired result of a particular biological process by regulating the nutrient composition added to such biological process in response to results from tests performed as to the effect of different nutrient composition additions to the biological process.

A device for determining nutrient limitations on growth and activity of microorganisms in an aqueous environment comprising holding means for holding a liquid nutrient medium for stimulating growth of the microorganisms, the holding means including nutrient-diffusing substrate means disposed on the holding means for gradually releasing an effective amount of the liquid nutrient medium such that the microorganisms are stimulated to attach to and grow on the nutrient-diffusing substrate means; and suspension means disposed on the holding means for suspending the device in the aqueous environment. The device preferably comprises a plurality of the holding means coupled together and spaced apart in a linear series by connecting means. Preferably the holding means comprises an impermeable cylindrical side wall, an impermeable top disposed on the side wall, and a porous bottom disposed on the side wall, the porous bottom comprising the nutrient-diffusing substrate means and the side wall, top, and bottom defining a cavity for holding the liquid nutrient medium.

The device preferably comprises means, such as a removable plug, for filling the cavity with the liquid nutrient medium. Also the porous bottom may be detachable from the side wall, and additionally the device may comprise means for sealing the porous bottom to the side wall.

The device preferably further comprises a gas sensor disposed thereon for monitoring a gas, such as oxygen and/or carbon dioxide, given off by the microorganisms attached to and growing on the nutrient-diffusing substrate means. The device may also comprise a computer linked to the gas sensor for receiving monitoring data generated by the gas sensor, which data may then be used to have the computer control the addition of nutrient composition to the biological system from which the data was generated.

A preferred device is one where the nutrient-diffusing substrate means comprises a porous ceramic support.

A method of determining nutrient limitations on growth of microorganisms in an aqueous environment comprising the steps of providing a device comprising holding means for holding a liquid nutrient medium for stimulating growth of the microorganisms, the holding means including nutrient-diffusing substrate means disposed on the holding means for gradually releasing an effective amount of the liquid nutrient medium such that the microorganisms are stimulated to attach to and grow on the nutrient-diffusing substrate means; and suspension means disposed on the holding means for suspending the device in the aqueous environment; placing a liquid nutrient medium to be tested in the holding means; suspending the device in the aqueous environment for a sufficient time for the nutrient-diffusing substrate means to gradually release the liquid nutrient medium such that the microorganisms attach to and grow on the nutrient-diffusing substrate means; and measuring growth of the microorganisms on the nutrient-diffusing substrate means. The method is especially appropriate when the aqueous environment comprises an aquifer.

As used herein, "aqueous environment" means an aqueous locale, such as an aquifer or water well, that a person skilled in this art might select for determining nutrient limitations on growth of microorganisms therein. Such microorganisms could be indigenous or introduced. The growth of such microorganisms would be important in biological processes such as bioremediation, biologically enhanced oil recovery, biological leaching of metals, biological treatment of compost, and the like.

As used herein, "liquid nutrient medium' means an aqueous solution containing a carbon source and energy source for supporting growth of microorganisms. These carbon and energy sources are not considered to be novel, but are conventional carbon sources and energy sources known in the art. Such carbon and energy sources include, without limitation, carbohydrates, organic acids, alcohols, nitrogenous compounds, phosphorous compounds, and the like.

As used herein, "effective amount" means an amount of a liquid nutrient medium sufficient to stimulate growth of microorganisms indigenous to or introduced to an aqueous environment.

DETAILED DESCRIPTION OF THE INVENTION

Figure 1:
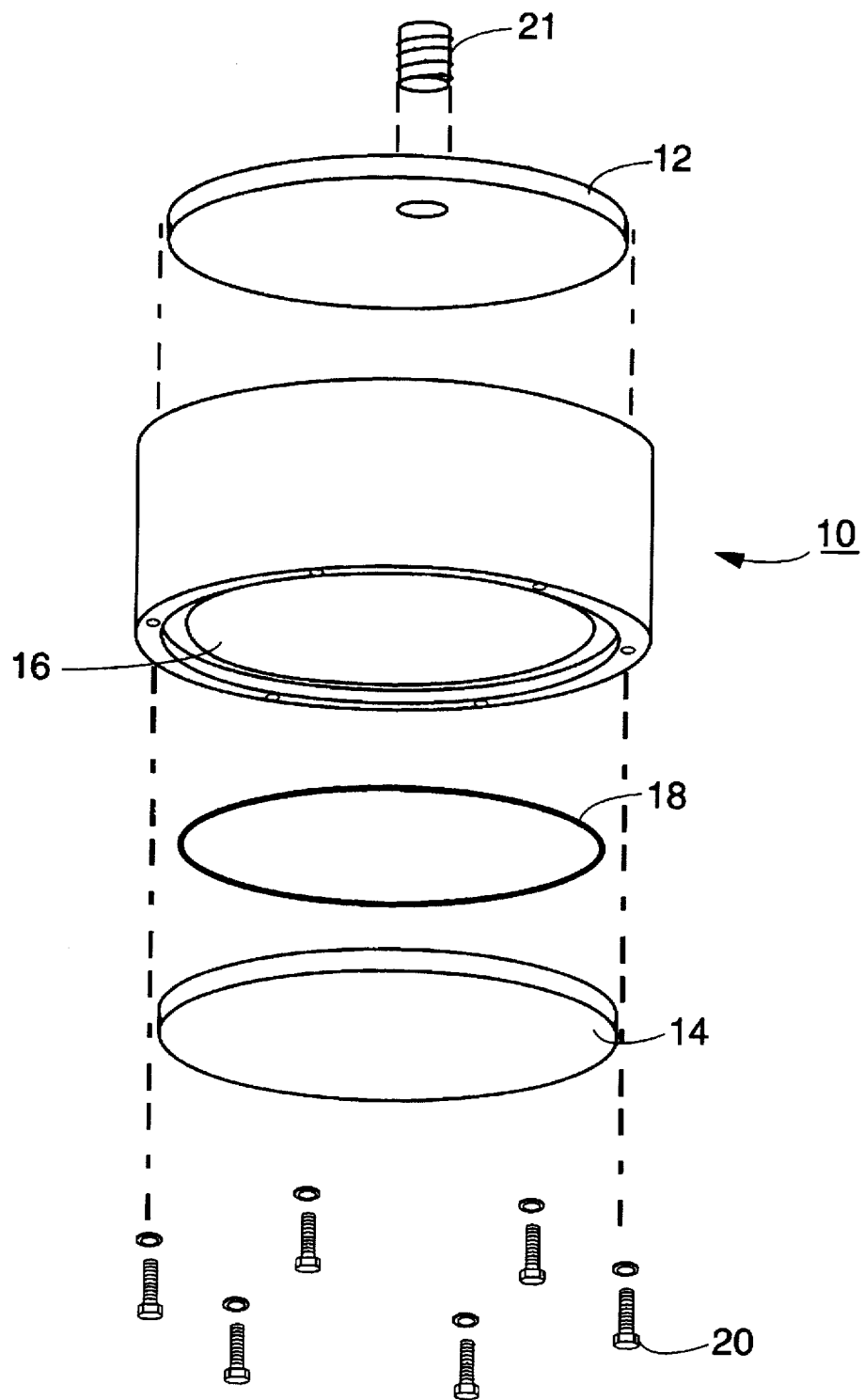
FIG. 1 is a cross-sectional view of a component of an apparatus according to the present invention, comprising a support means and a container, to be filled with a nutrient solution, to be tested for possible application to a biological process, according to a preferred embodiment of the invention.

Referring now to FIG. 1., the apparatus in its preferred embodiment comprises a cylinder 10, preferably cylindrical in shape, with a nonporous lid 12 and a porous bottom surface 14, that, when assembled with 10, form a container with a cavity 16. The assembled unit is made to hold a solution or gel in cavity 16 which contains one or more nutrients that are intended to diffuse through the porous surface 14. The nonporous lid 12 and cylinder 10 may be machined separately or from a single unit. An "O" ring 18 seals the gap between the cylinder 10 and the porous surface 14 and the porous surface is secured to the cylinder using bolts 20. A plug 21 is present in the nonporous lid 12 to provide a hole through which the solution or gel can be poured. The entire assembly is composed of materials that can be sterilized, preferably in an autoclave, prior to use. The dimensions of the assembled unit must be such that it can fit into the borehole of interest, allowing it to be suspended beneath the level of the water table.

The porous surface 14 is the surface upon which microorganisms grow or are active and such microorganisms can be monitored using sensors attached to porous base 14 or after the device is contacted with a representative sample for a period of time sufficient to measure differences in the microorganism effects. The porous surface 14 can be scraped to acquire and measure the microorganisms that have become attached.

Figure 2:
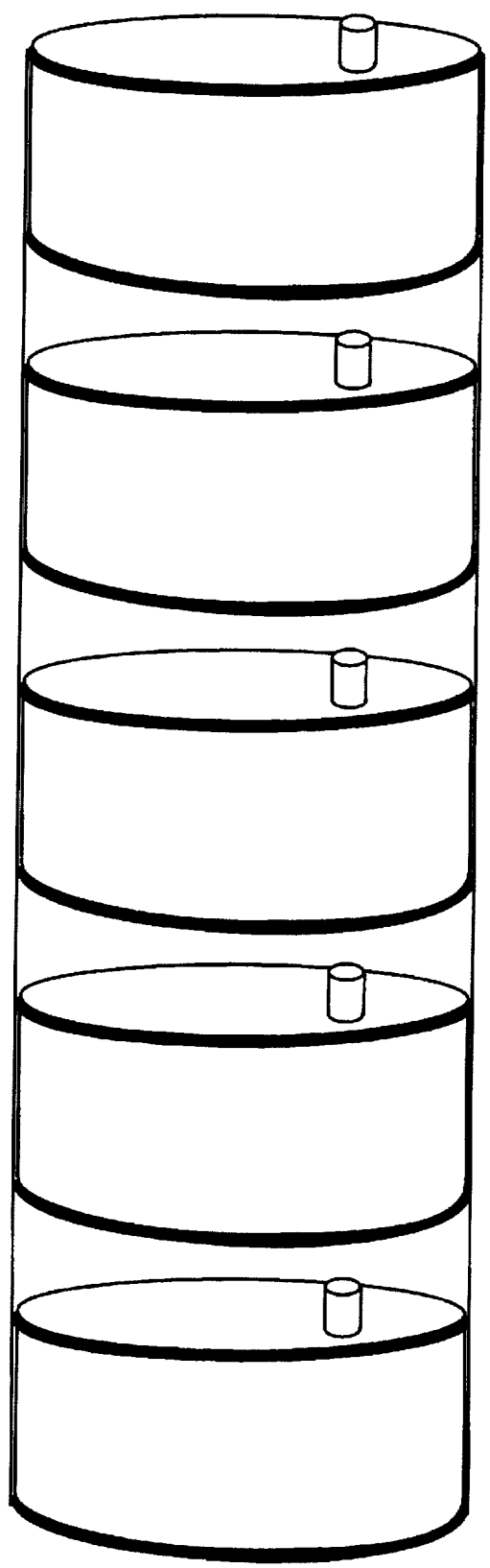
FIG. 2 is a view of the apparatus of this present invention comprising multiple components such as the one shown in FIG. 1, attached to each other, according to a preferred embodiment of the present invention.

In FIG. 2, several of the preferred components shown in FIG. 1. are connected in sequence as they would be when suspended by a cable to a position beneath the level of the water table in an aquifer. Incubation within the aquifer occurs in this manner for a period of time necessary to measure differences in the microorganisms on the porous surface of the different components. Each of the preferred embodiments contains a different nutrient or different concentrations of the same nutrient.

The invention is further illustrated by the following non-limiting examples.

EXAMPLE 1

Figure 3:
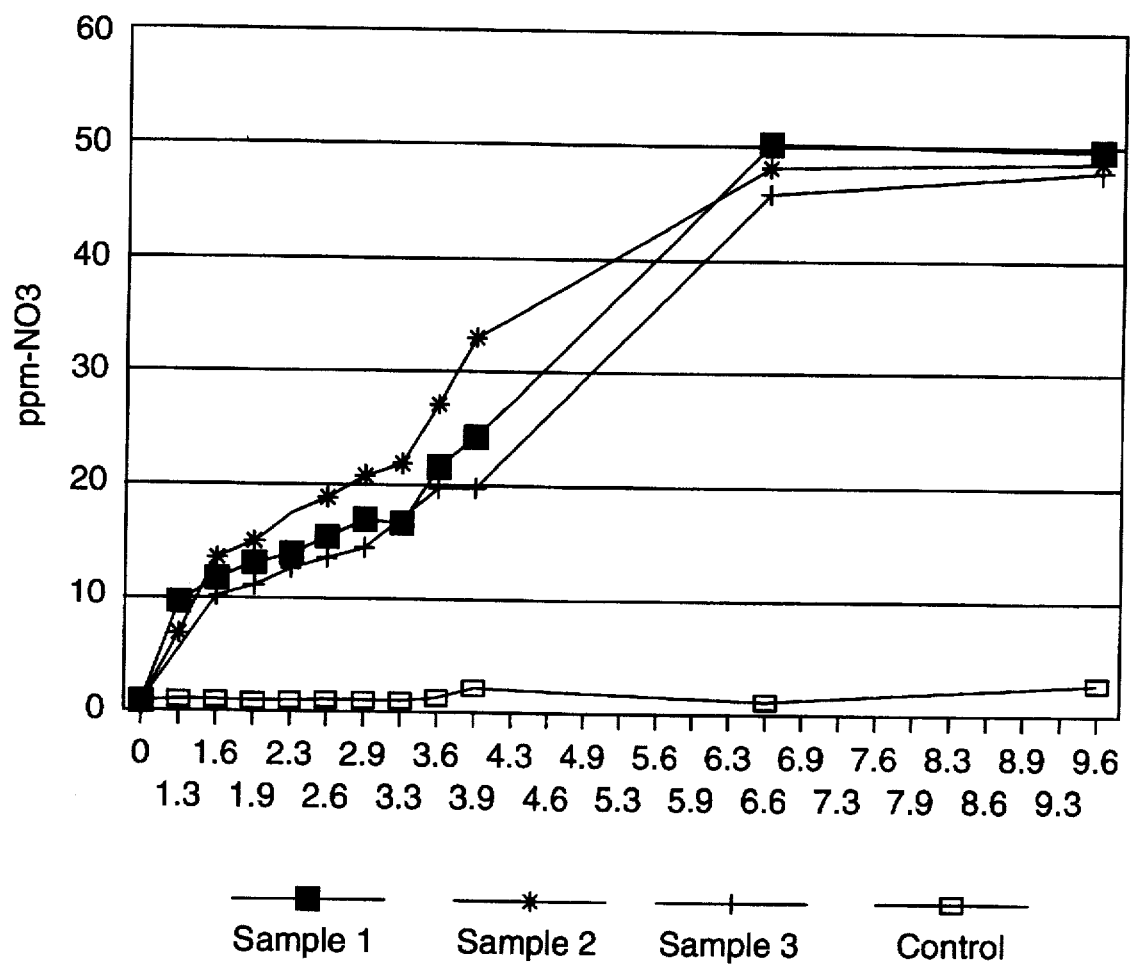
FIG. 3 is a graph showing the diffusion of nitrate from a component such as shown in FIG. 1 of the invention under batch conditions with no microorganisms present.

The concentration of nitrate measured with respect to time in replicated 2 liter vessels similar to FIG. 1, each containing sterile aquifer water and a single nitrate-containing nutrient composition is depicted in FIG. 3. Nitrate in the aqueous phase of the vessels was measured using ion chromatography. Increasing time results in progressively higher levels of nitrate in the sterile aquifer water thus demonstrating the effectiveness of the invention for allowing gradual diffusion of an inorganic microbial nutrient through the porous surface.

EXAMPLE 2

Figure 4:
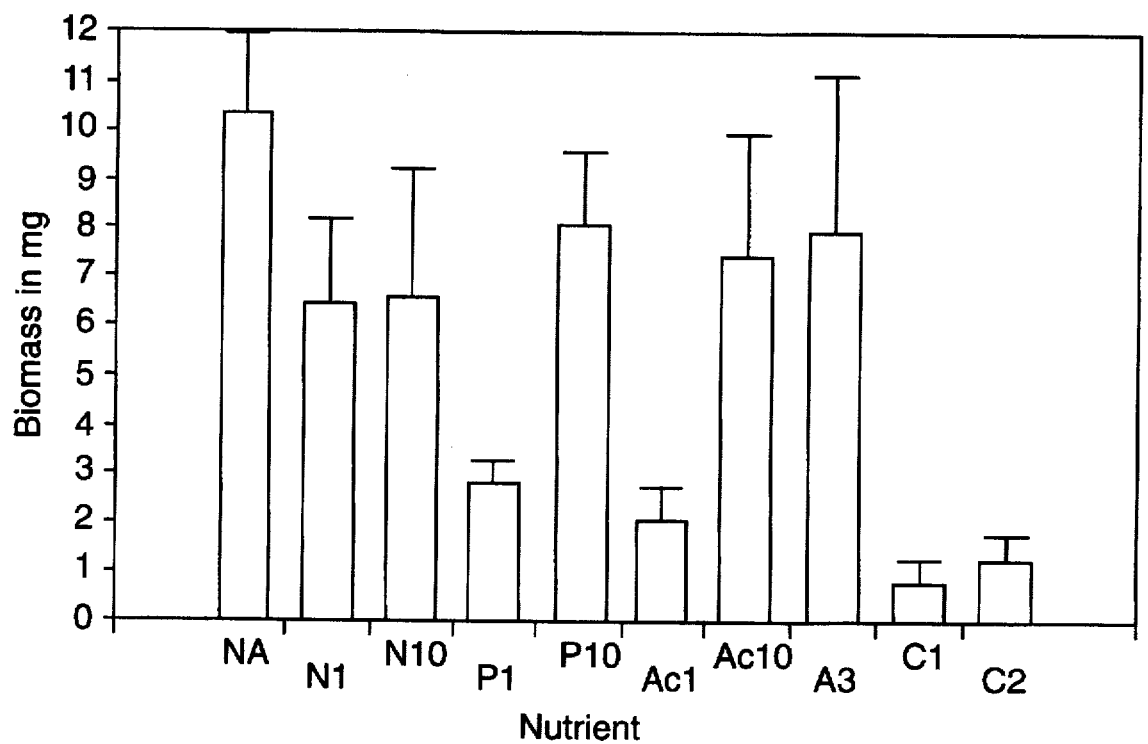
FIG. 4 is a graph showing the relationship of biomass produced on the porous surface of a component such as shown in FIG. 1 relative to the nutrients supplied within the component.

A chart is shown in FIG. 4, which depicts the quantity of biomass obtained from individual porous surfaces of the apparatus shown in FIG. 2, after a 12 day in situ aquifer experiment. The designations for nutrients in the different component vessels of the apparatus of FIG. 1 are as shown in FIG. 4 are as follows: C1 and C2: both control without nutrients; N1: 1500 mg nitrate/L; N10: 15000 mg nitrate/L;

P1: 93 mg trimetaphosphate/L; P10: 930 mg trimetaphosphate/L; Ac1: 100 mg acetate/L; Ac10: 1000 mg acetate/L; A3: acetate, nitrate and trimetaphosphate added in 1000:143:9 C:N:P ratios; NA: nutrient agar. With the exception of nitrate, treatments with lower concentrations of inorganic or organic nutrients allowed only limited quantities of biomass to develop on the porous surfaces. Control components exhibited markedly lower levels of attached biomass than all other components, although P1 (93 mg trimetaphosphate/L) and Ac1 (100 mg acetate/L) were comparable. It is not possible to distinguish between samples that contained the highest concentration of nutrients (N10, P10, Ac10, A3 and NA) and there is an indication that in this aquifer microorganisms are limited mainly by nitrate since even the lowest concentration of nitrate (N1 at 1500 mg nitrate/L) caused a significant increase in biomass above controls. These results provide evidence that subsurface microorganisms which become attached to the porous surfaces respond favorably to nutrient enrichment.

EXAMPLE 3

Figure 5:
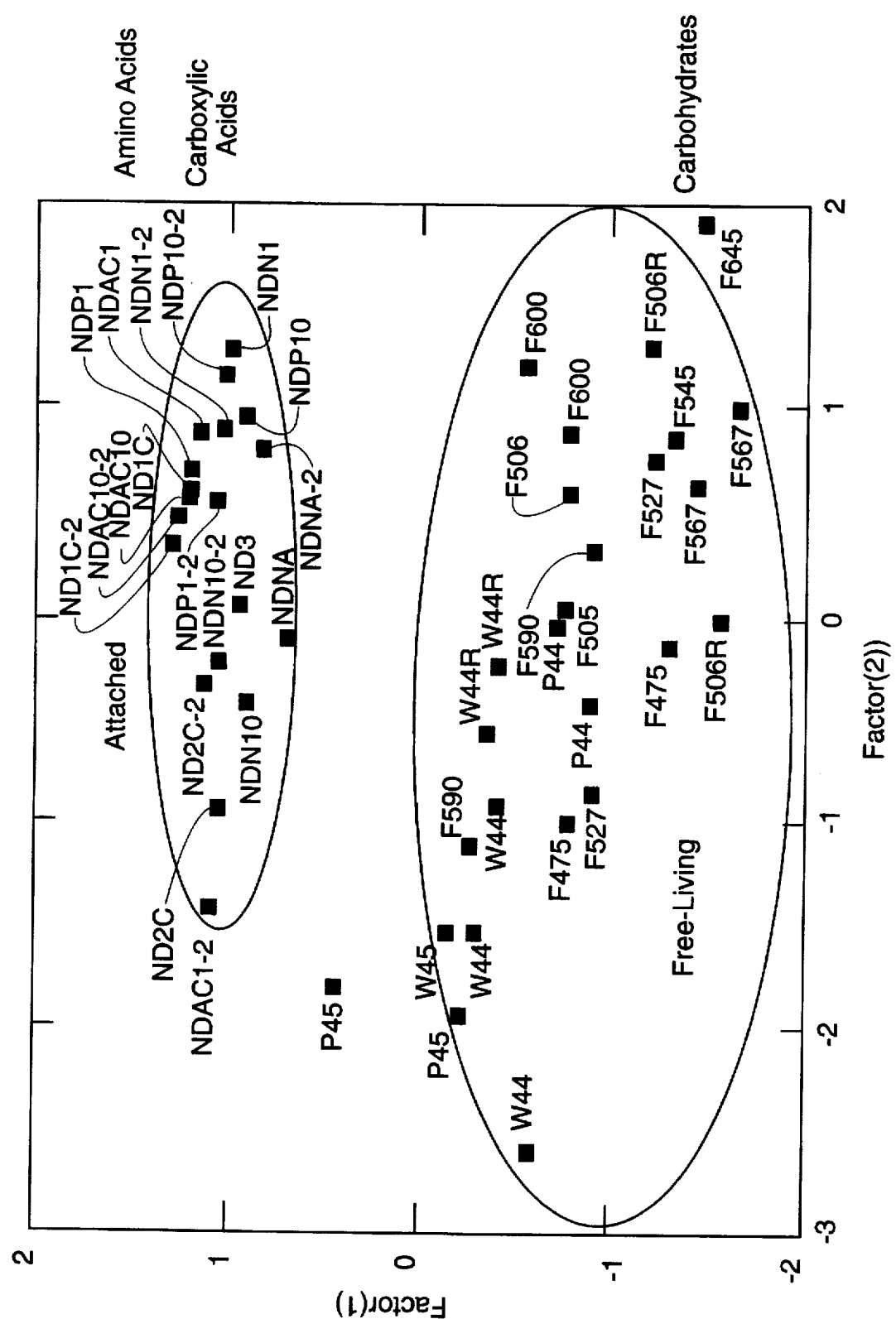
FIG. 5 is a graph showing the results of principal components analysis which compares the results obtained from attached microbial communities to free-living microbial communities from the same aquifer.

FIG. 5 shows a chart depicting the results of a multiple carbon source utilization assay conducted on microbial communities obtained from the porous surfaces of the apparatus depicted in FIG. 1 compared to the results of the same assay performed on free-living microbial communities from the same aquifer. The data obtained for the utilization of 95 different organic carbon sources by the microbial communities was analyzed using principal component analysis. These data indicate that the porous surface upon which cells adhere allows the development of a microbial community unique from that in the liquid phase. The results also suggest that the microbial communities that were attached to the porous surface of the present embodiment of the invention preferred to use amino acids and carboxylic acids relative to the free-living microorganisms from the same aquifer which preferred to use carbohydrates. Attached microbial communities in aquifers are numerically and functionally dominant and the invention described herein is designed to select for these communities as distinct from prior art.

We claim:

1. A device for determining the nutrient limitations on growth of microorganisms in an aqueous environment comprising a. holding means for holding a liquid nutrient medium for stimulating growth of said microorganisms, said holding means including nutrient-diffusing substrate means disposed on said holding means for gradually releasing an effective amount of said liquid nutrient medium such that said microorganisms are stimulated to attach to and grow on said nutrient-diffusing substrate means; and b. suspension means disposed on said holding means for suspending said device in said aqueous environment.

2. The device of claim 1 comprising a plurality of said holding means coupled together and spaced apart in a linear series by connecting means.

3. The device of claim 2 wherein said holding means comprises an impermeable cylindrical side wall, an impermeable top disposed on said side wall, and a porous bottom disposed on said side wall consisting of said nutrient-diffusing substrate means, said side wall, top, and bottom defining a cavity for holding said liquid nutrient medium.

4. The device of claim 3 further comprising means for filling said cavity with said liquid nutrient medium.

5. The device of claim 4 wherein said filling means comprises a removable plug.

6. The device of claim 3 wherein said porous bottom is detachable from said side wall and wherein said device further comprises means for sealing said porous bottom to said side wall.

7. The device of claim 1 wherein said device further comprises a gas sensor disposed thereon for monitoring a gas given off by said microorganisms attached to and growing on said nutrient-diffusing substrate means.

8. The device of claim 7 wherein said gas sensor monitors oxygen gas.

9. The device of claim 7 wherein said gas sensor monitors carbon dioxide gas.

10. The device of claim 7 wherein said gas sensor monitors a mixture of oxygen gas and carbon dioxide gas.

11. The device of claim 7 further comprising a computer linked to said gas sensor for receiving monitoring data generated by said gas sensor.

12. The device of claim 1 wherein said nutrient-diffusing substrate means comprises a porous ceramic support.

* * * * *